(12) United States Patent
Gardlik et al.

(10) Patent No.: US 9,309,185 B2
(45) Date of Patent: *Apr. 12, 2016

(54) PROCESS FOR PREPARING PRIMARY INTERMEDIATES FOR DYEING KERATIN FIBERS

(71) Applicant: The Procter & Gamble Company, Cincinnati, OH (US)

(72) Inventors: John Michael Gardlik, Cincinnati, OH (US); Monica Jo Patten, West Chester, OH (US); Garry Steven Garrett, Fairfield, OH (US); Bryan Patrick Murphy, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/063,560

(22) Filed: Oct. 25, 2013

(65) Prior Publication Data

US 2014/0121415 A1 May 1, 2014

Related U.S. Application Data

(60) Provisional application No. 61/718,961, filed on Oct. 26, 2012.

(51) Int. Cl.
| | | |
|---|---|---|
| C07C 209/00 | (2006.01) |
| C07C 213/02 | (2006.01) |
| C07C 213/00 | (2006.01) |
| C07C 213/06 | (2006.01) |

(52) U.S. Cl.
CPC ............. *C07C 213/02* (2013.01); *C07C 213/00* (2013.01); *C07C 213/06* (2013.01)

(58) Field of Classification Search
CPC .................................................. C07C 213/02
See application file for complete search history.

(56) References Cited

U.S. PATENT DOCUMENTS

| | | | |
|---|---|---|---|
| 2,273,564 A | 2/1942 | Dickey | |
| 2,528,378 A | 10/1950 | Mannheimer | |
| 2,781,354 A | 2/1957 | Mannheimer | |
| 4,976,742 A | 12/1990 | Rose | |
| 4,997,451 A | 3/1991 | Clausen | |
| 6,503,282 B1 | 1/2003 | Braun | |
| 6,648,923 B1 | 11/2003 | Goettel | |
| 7,591,860 B2 | 9/2009 | Sabelle | |
| 7,985,266 B2 | 7/2011 | Zhang | |
| 7,988,740 B2 | 8/2011 | Zhang | |
| 8,444,709 B2 | 5/2013 | Lim | |
| 8,444,710 B2 | 5/2013 | Lim | |
| 8,444,711 B2 | 5/2013 | Lim | |
| 8,444,712 B2 | 5/2013 | Lim | |
| 8,444,713 B2 | 5/2013 | Lim | |
| 8,444,714 B2 | 5/2013 | Lim | |
| 8,460,397 B2 | 6/2013 | Lim | |
| 9,012,691 B2 * | 4/2015 | Gardlik et al. | 564/420 |
| 2010/0063037 A1 * | 3/2010 | Kolczewski et al. | 514/228.2 |
| 2012/0078016 A1 | 3/2012 | Gardlik | |
| 2012/0130128 A1 | 5/2012 | Goettel | |
| 2012/0142969 A1 | 6/2012 | Gardlik | |
| 2013/0081647 A1 | 4/2013 | Vohra | |

FOREIGN PATENT DOCUMENTS

| | | |
|---|---|---|
| CA | 2576189 A1 | 6/2007 |
| DE | 20107481 U1 | 7/2001 |
| DE | 102008061864 A1 | 10/2010 |
| EP | 1166749 B1 | 10/2005 |
| EP | 1765267 B1 | 1/2010 |
| FR | 2946648 A1 | 12/2010 |
| FR | 2945726 B1 | 6/2011 |
| FR | 2945731 B1 | 6/2011 |
| FR | 2945732 B1 | 6/2011 |
| FR | 2945734 B1 | 6/2011 |
| FR | 2945735 B1 | 6/2011 |
| FR | 2945736 B1 | 6/2011 |
| FR | 2945737 B1 | 6/2011 |
| FR | 2945740 B1 | 6/2011 |
| FR | 2945741 B1 | 6/2011 |
| FR | 2945744 B1 | 6/2011 |
| FR | 2946647 B1 | 6/2011 |
| FR | 2945738 B1 | 7/2011 |
| FR | 2945739 B1 | 7/2011 |
| FR | 2945756 B1 | 8/2011 |
| FR | 2945727 B1 | 8/2012 |
| FR | 2945733 B1 | 8/2012 |
| FR | 2945742 B1 | 8/2012 |
| FR | 2945743 B1 | 9/2012 |
| FR | 2945728 B1 | 10/2012 |
| FR | 2945729 B1 | 10/2012 |
| FR | 2945730 B1 | 10/2012 |
| WO | WO2010133573 A2 | 11/2010 |
| WO | WO2010133575 A2 | 11/2010 |
| WO | WO2010133639 A1 | 11/2010 |
| WO | WO2010133640 A2 | 11/2010 |
| WO | WO2010133803 A1 | 11/2010 |
| WO | WO2010133804 A2 | 11/2010 |
| WO | WO2010133805 A1 | 11/2010 |
| WO | WO2010139878 A2 | 12/2010 |
| WO | WO2010142776 A1 | 12/2010 |
| WO | WO2010142777 A1 | 12/2010 |

OTHER PUBLICATIONS

Encyclopedia of Chemical Technology, Kirk-Othmer, Third Edition, 1982, vol. 3, pp. 896-900.
Encyclopedia of Chemical Technology, Kirk-Othmer, Third Edition, 1982, vol. 15, pp. 439-458.
Polymers in Nature by E. A. MacGregor and C. T. Greenwood, published by John Wiley & Sons, Chapter 6, pp. 240-328,1980.
Handbook of Surfactants by M. R. Porter, published by Blackie & Son (Glasgow and London), 1991, pp. 116-178.
Whistler, Roy L., Editor, "Industrial Gums—Polysaccharides and their Derivatives," Academic Press, Inc. 1993.
Yoshihiro Ida; Synthesis of quinolinomorphinan derivatives as highly selective δ opioid receptor ligands; Biorganic & Medical Chemistry 20 (2012) 5810-5831.
Akio Kamimura; A study on the relationship between the twisted π-conjugate system of 1,5-diaryl-1,5-diazapenta-1,3-dienes and their photophysical properties; Chem. Lett 2012, 41, 984-986; The Chemical Society of Japan.

* cited by examiner

*Primary Examiner* — Clinton Brooks
(74) *Attorney, Agent, or Firm* — James T. Fondriest

(57) ABSTRACT

A process has been developed for preparing 2-methoxymethyl-1,4-benzenediamine (IV-a), other compounds of formula (IV), and the salts thereof, all of which may be used as primary intermediates in compositions for dyeing keratin fibers.

18 Claims, No Drawings

PROCESS FOR PREPARING PRIMARY INTERMEDIATES FOR DYEING KERATIN FIBERS

FIELD OF THE INVENTION

The present invention relates to a process for preparing primary intermediates for dyeing keratin fibers. More particularly, the invention relates to a process for preparing 2-methoxymethyl-1,4-benzenediamine (IV-a), other compounds of formula (IV), and the salts thereof.

BACKGROUND OF THE INVENTION

Primary intermediates are used in compositions for dyeing keratin fibers. Known primary intermediates include 2-methoxymethyl-1,4-benzenediamine (IV-a), other compounds of formula (IV), and the salts thereof.

Known processes of preparing 2-methoxymethyl-1,4-benzenediamine (IV-a), other compounds of formula (IV), and the salts thereof have yield and cost deficiencies. Therefore, there is a need for an industrially applicable, less expensive, and higher yielding process to synthesize 2-methoxymethyl-1,4-benzenediamine (IV-a), other compounds of formula (IV), and the salts thereof.

SUMMARY OF THE INVENTION

According to one embodiment of the invention, there is provided a process for the preparation of 2-methoxymethyl-1,4-benzenediamine (IV-a), other compounds of formula (IV), and the salts thereof comprising (a) performing a carbonyl reduction of a compound of formula (I) to prepare a compound of formula (II); (b) performing an etherification of the compound of formula (II) to prepare a compound of formula (III); and (c) performing a hydrogenation of the compound of formula (III) to prepare a compound of formula (IV):

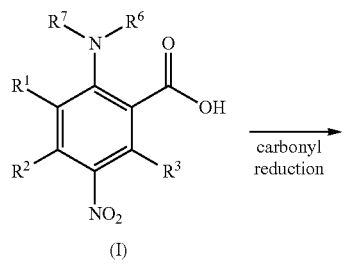

(I)

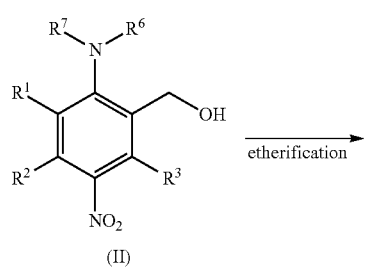

(II)

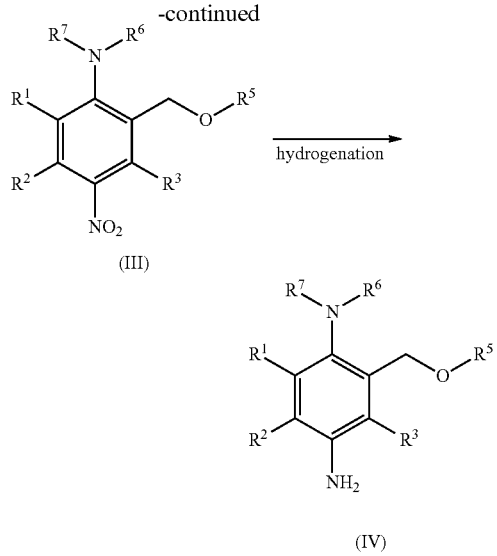

(IV-a), $R^1, R^2, R^3, R^6, R^7 = H$
$R^5 = CH_3$ wherein $R^1$, $R^2$, and $R^3$ are substituents selected from the group consisting of:
  a) C-linked substituents selected from the group consisting of:
    i. alkyl groups;
    ii. aryl groups; and
    iii. substituents selected from the group consisting of $COOA^1$, $CONA^1$, $CONA^1COA^2$, $C(=NA^1)NA^1A^2$, and $CN$;
      wherein the C-linked substituents comprise from 1 to about 10 carbon atoms and from 0 to about 5 heteroatoms selected from the group consisting of O, F, Cl, N, P, Si, and mixtures thereof;
  b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
  c) O-linked substituents selected from the group consisting of $OA^1$, $ONA^1A^2$;
  d) N-linked substituents selected from the group consisting of $NA^1A^2$; $(NA^1A^2A^3)^+$, $NA^1SA^2$, $NO_2$;
  e) halogens selected from the group consisting of F, Cl, Br, and I;
  f) hydrogen; and
  g) mixtures thereof;
    wherein $A^1$, $A^2$, and $A^3$ are alkyl groups comprising from 1 to about 10 carbon atoms and from 0 to about 5 heteroatoms selected from the group consisting of O, F, Cl, N, P, Si, and mixtures thereof;
  wherein $R^5$ is an alkyl group; and
  wherein $R^6$ and $R^7$ are selected from the group consisting of hydrogen, alkyl groups, aminoalkyl groups, hydroxyalkyl groups, and mixtures thereof.

This and other features, aspects, and advantages of the present invention will become evident to those skilled in the art from a reading of the present disclosure.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "comprising," as used herein, means that other steps and other ingredients which do not affect the end result can be added. This term encompasses the terms "consisting of" and "consisting essentially of." Compositions and methods/processes of the present invention can comprise, consist of, and consist essentially of the elements and limitations of the invention described herein, as well as any of the additional or optional ingredients, components, steps, or limitations described herein.

The terms "include," "includes," and "including," as used herein, are meant to be non-limiting and are understood to mean "comprise," "comprises," and "comprising," respectively. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The process for the preparation of 2-methoxymethyl-1,4-benzenediamine (IV-a), other compounds of formula (IV), and the salts thereof comprises (a) performing a carbonyl reduction of a compound of formula (I) to prepare a compound of formula (II); (b) performing an etherification of the compound of formula (II) to prepare a compound of formula (III); and (c) performing a hydrogenation of the compound of formula (III) to prepare a compound of formula (IV).

In an embodiment, the carbonyl reduction, then etherification, and then hydrogenation may be performed successively. In another embodiment, the carbonyl reduction, then hydrogenation, and then etherification may be performed successively.

I. Carbonyl Reduction

Carbonyl reduction may be performed on a compound of formula (I) to prepare a compound of formula (II). $R^1$, $R^2$, $R^3$, $R^6$, and $R^7$ are as defined previously, may be independently selected, and may be identical or different. Carbonyl reduction may be performed in the presence of a carbonyl reducing agent, a carbonyl reduction catalyst, and/or a solvent.

The carbonyl reducing agent may be selected from the group consisting of hydrazine, hydrazine hydrate, $H_2$, $LiAlH_4$, $LiBH_4$, DIBAL-H, $NaBH_4$, $NaCNBH_3$, $B_2H_6$, $BH_3$/THF, sodium hydrosulfite, sodium sulfide, and mixtures thereof.

The carbonyl reduction catalyst may be selected from the group consisting of Raney nickel, nickel, palladium, Lindlar's catalyst, cobalt, copper chromite, platinum, platinum oxide, rhenium, tin(II) chloride, titanium(III) chloride, zinc, samarium, iron, ruthenium, iridium, rhodium, and mixtures thereof.

The solvent may be selected from the group consisting of water, petroleum ether, pentane, acetic acid, cyclopentane, hexane, cyclohexane, benzene, toluene, 1,4-dioxane, chloroform, diethyl ether, dichloromethane, tetrahydrofuran, methyl-tetrahydrofuran, dimethylformamide, acetonitrile, dimethyl sulfoxide, n-butanol, isopropanol, n-propanol, ethanol, methanol, and mixtures thereof.

Carbonyl reduction may be carried out at a temperature of from about 0° C. to about 100° C., alternatively from about 50° C. to about 80° C., alternatively at about 70° C.

In an embodiment, the formula indicated by formula (I) may be prepared by inserting a nitro function into anthranilic acid or compounds thereof in the presence of a nitrating agent and/or a solvent. The nitrating agent may be selected from the group consisting of nitric acid, fuming nitric acid, red fuming nitric acid, salts of nitric acid (i.e. potassium nitrate), and mixtures thereof.

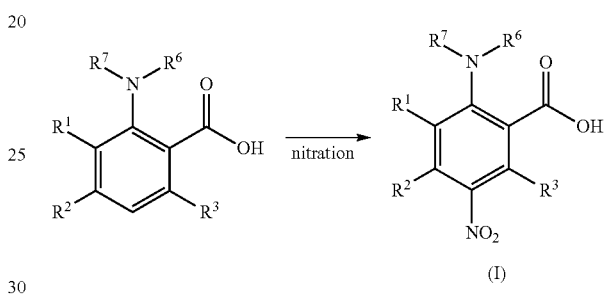

(I)

II. Etherification

Etherification may be performed on the compound of formula (II) to prepare a compound of formula (III). $R^1$, $R^2$, $R^3$, $R^5$, $R^6$, and $R^7$ are as defined previously, may be independently selected, and may be identical or different.

Alkylation Reaction

Etherification may be performed by an alkylation reaction in the presence of an alkylating agent, a phase transfer catalyst, a solvent, and/or a base. The reaction mixture may be homogeneous or heterogeneous, may have two or more liquid phases, and/or may have any combination of liquid and solid phases.

The alkylating agent may be selected from the group consisting of alcohols, derivatives of alcohols (i.e. methyl methanesulfonate), $(C_1$-$C_4)$—I, $(C_1$-$C_4)$—Br, $(C_1$-$C_4)$—Cl, $Me_2SO_4$, and mixtures thereof. In one embodiment, the alkylating agent may be dimethyl sulfate.

The phase transfer catalyst may be selected from the group consisting of ammonium salts that include tetrapentylammonium bromide, tetraoctylammonium chloride, tetraoctylammonium bromide, tetrahexylammonium iodide, tetrahexylammonium chloride, tetrahexylammonium bromide, tetraheptylammonium bromide, tetraethylammonium tetrafluoroborate, tetraethylammonium chloride, tetraethyl ammonium bromide, tetradodecylammonium tetrafluoroborate, tetradodecylammonium chloride, tetradodecylammonium bromide, tetradecyl-trimethylammonium chloride, benzyltriethyl ammonium chloride, phenyl-trimethylammonium bromide, octyl-trimethylammonium bromide, octadecyl-trimethylammonium chloride, octadecyl-trimethylammonium bromide, methyl-trioctylammonium iodide, and mixtures thereof. In one embodiment, the phase transfer catalyst may be benzyltriethyl ammonium chloride.

The solvent may be selected from the group consisting of water, petroleum ether, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol, and mixtures thereof.

The base may be selected from the group consisting of sodium hydroxide, potassium hydroxide, ammonium hydroxide, calcium hydroxide, magnesium hydroxide, barium hydroxide, aluminum hydroxide, ferrous hydroxide, ferric hydroxide, zinc hydroxide, lithium hydroxide, sodium bicarbonate, sodium carbonate, and mixtures thereof. In one embodiment, the base may be sodium hydroxide.

Condensation Reaction

Etherification may also be performed by a condensation reaction in the presence of a condensation catalyst and/or a solvent.

The condensation catalyst may be selected from the group consisting of mineral acids, Lewis Acids, aluminum chloride, titanium tetra-isopropoxide, and mixtures thereof.

The solvent may be selected from the group consisting of petroleum ether, pentane, cyclopentane, hexane, acetic acid, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol, and mixtures thereof. In one embodiment, the solvent may be methanol.

The condensation reaction may be carried out with an inert solvent diluent and/or with heating. The inert solvent diluent may be chosen to aid in the removal of water if it is capable of forming a low boiling azeotrope. In this case, the condensation reaction may be carried out at reflux using a Dean Stark trap to drain off the water as it is formed and distilled off with the azeotrope. The condensation reaction may also be carried out in the presence of one or more dehydrating agents which may either react with or physically bind with the water, thereby removing the water from equilibria. The dehydrating agent may be selected from the group consisting of dicyclohexylcarbodiimide, molecular sieves, magnesium sulphate, and mixtures thereof.

III. Hydrogenation

Hydrogenation may be performed on the compound of formula (III) to prepare a compound of formula (IV). $R^1$, $R^2$, $R^3$, $R^5$, $R^6$, and $R^7$ are as defined previously, may be independently selected, and may be identical or different.

Hydrogenation may be performed in the presence of hydrogen, a hydrogenation catalyst, and/or a solvent. The hydrogenation catalyst may be selected from the group consisting of Raney nickel, nickel, palladium, Lindlar's catalyst, cobalt, copper chromite, platinium, platinum oxide, rhenium, tin(II) chloride, titanium(III) chloride, zinc, samarium, iron and mixtures thereof. The hydrogen pressure may be in a range from about atmospheric pressure to about 2,000 psig, alternatively from about 50 psig to about 60 psig.

The solvent may be selected from the group consisting of water, petroleum ether, pentane, cyclopentane, hexane, cyclohexane, benzene, toluene, 1,4-dioxane, chloroform, diethyl ether, dichloromethane, tetrahydrofuran, methyl-tetrahydrofuran, ethyl acetate, acetone, dimethylformamide, acetonitrile, dimethyl sulfoxide, n-butanol, isopropanol, n-propanol, ethanol, methanol. and mixtures thereof. In an embodiment, the solvent may be ethyl acetate.

In an embodiment, the compound of formula (IV) may be transformed into the salt of formula (V) in the presence of mHZ and a solvent. $R^1$, $R^2$, $R^3$, $R^5$, $R^6$, and $R^7$ are as defined previously, may be independently selected, and may be identical or different.

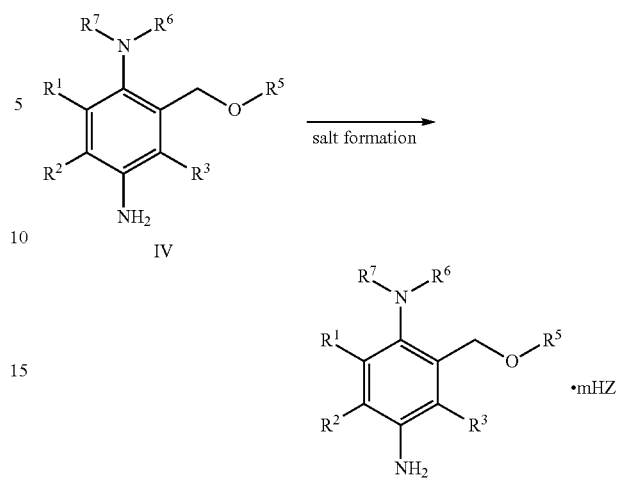

HZ is an acid having an acid proton "H." "Z" represents the rest of the molecule. For example if HZ=HCl, then Z=Cl. The symbol "m" is the number of moles of the acid. HZ may be selected from the group consisting of D,L-malic acid, L-malic acid, D-malic acid, hydrochloric acid, hydrobromic acid, citric acid, acetic acid, lactic acid, succinic acid, tartaric acid, sulfuric acid, and mixtures thereof; and m may be ½, 1, 3/2, or 2.

Protecting Groups

In an embodiment, a protecting group may be used when performing the above process. Protecting groups are widely used in chemistry and one skilled in the art would determine the appropriate step during the process to remove the protecting group in order to reach compounds of formula (IV). General explanations and uses of protecting groups are described in "Greene's Protective Groups in Organic Synthesis" by Peter G. M. Wuts, Theodora W. Greene, Wiley-Interscience; 4th edition (Oct. 30, 2006) and in "Protecting Groups" by Philip J. Kocienski, Thieme, Stuttgart; Auflage: 3rd Revised edition (Feb. 14, 2005).

IV. Synthesis of 2-Methoxymethyl-1,4-Benzenediamine

Compounds of formula (IV) include 2-methoxymethyl-1,4-benzenediamine (IV-a). The process described above can be utilized to synthesize 2-methoxymethyl-1,4-benzenediamine (IV-a). The process may comprise:

a) reducing the carbonyl group of 5-nitroanthranilic acid (I-a) to prepare 2-amino-5-nitrobenzyl alcohol (II-a);

b) performing the etherification of 2-amino-5-nitrobenzyl alcohol (II-a) to prepare 2-methoxymethyl-4-nitroaniline (III-a); and c) hydrogenating 2-methoxymethyl-4-nitroaniline (III-a) to prepare 2-methoxymethyl-1,4-benzenediamine (IV-a).

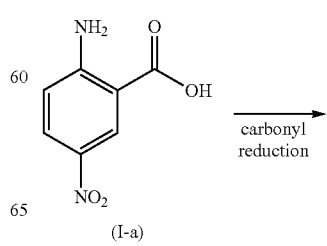

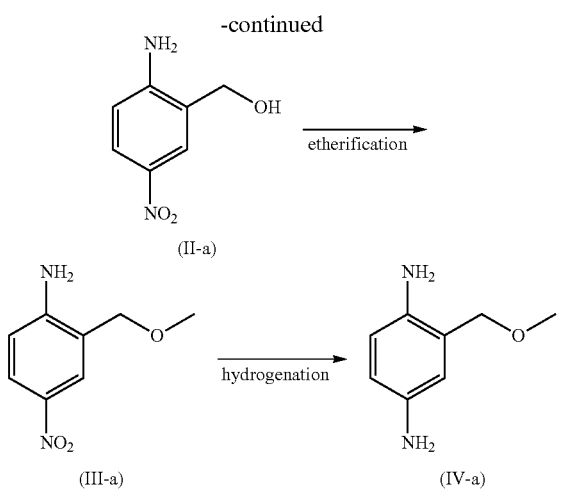

EXAMPLES

The following examples illustrate the present invention:

Example 1

1. Synthesis of 2-Hydroxymethyl-4-Nitroaniline (II-a)

5-Nitroanthranilic acid (5.0 g, 27.45 mmol) is dissolved in THF (100 mL) and 1 M borane/THF complex (55 mL, 54.9 mmol) is added. The mixture is heated to reflux for 1 h. Analysis by TLC indicates complete consumption of starting material. The volatiles are removed in vacuo and the residue is dissolved in ethyl acetate (150 mL). The organic phase is washed with 1 N HCl, saturated $NaHCO_3$, and saturated NaCl. Evaporation provides 10.8 g (98%) of a dark brown oil product which is used directly in the next reaction; $^1$H-NMR (500 MHz, $CDCl_3$); δ 4.61 (s, 2 H), 6.62 (s, 1 H), 8.01 (m, 2 H).

2. Synthesis of 2-Methoxymethyl-4-Nitroaniline (III-a)

2-Hydroxymethyl-4-nitroanilne (1.0 g, 5.75 mmol) is suspended in petroleum ether (10 mL). Sodium hydroxide solution (50%, 618 mg, 15.46 mmol) and benzyltriethylammonium chloride (20 mg) are added with stirring. Dimethyl sulfate (728 uL, 7 7 mmol) is added and the reaction mixture is stirred at room temperature for 16 hours. Dichloromethane (50 mL) and water (25 mL) are added, and the layers are separated. The organic layer is washed with saturated $NaHCO_3$ and evaporated affording 440 mg of 2-methoxymethyl-4-nitroaniline (III-a) in 82% purity.

3. Synthesis of 2-Methoxymethyl-1,4-Benzenediamine (IV-a)

Into a Parr hydrogenation bottle previously purged with argon, are placed a solution of 2-methoxymethyl-4-nitroaniline (5.0 g, 27.5 mmol) in ethyl acetate (50 mL) and 0.25 g of 10% palladium on carbon. The bottle is mounted on a Parr shaker and hydrogenation is carried out under 50-60 psig (64.7-74.7 psi or 446-515 kPa) of hydrogen pressure. The pressure is carefully monitored for hydrogen uptake and additional hydrogen is introduced to keep the pressure above 50 psig. The hydrogenation is carried out for 3.5 hours after which the catalyst is removed by vacuum filtration. The filtrate is concentrated to about 25 mL and toluene (25 mL) is added to precipitate the product, which is collected by vacuum filtration and dried at 60° C. under vacuum. The product yield is 4.5 g; $^1$H-NMR (500 MHz, DMSO-$d_6$) δ 3.23 (s, 3 H), 4.11 (s, 2 H), 4.21 (s, 2 H), 4.24 (s, 2 H), 6.33 (dd, 1 H), 6.37 (d, 1 H), 6.41 (d, 1 H).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover all such changes and modifications that are within the scope of this invention.

What is claimed is:
1. A process for the preparation of 2-methoxymethyl-1,4-benzenediamine (IV-a), other compounds of formula (IV), and the salts thereof comprising:
 a. performing a carbonyl reduction of a compound of formula (I) to prepare a compound of formula (II);
 b. performing an etherification of the compound of formula (II) to prepare a compound of formula (III); and
 c. performing a hydrogenation of the compound of formula (III) to prepare a compound of formula (IV);

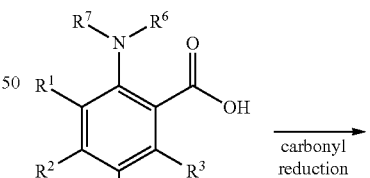

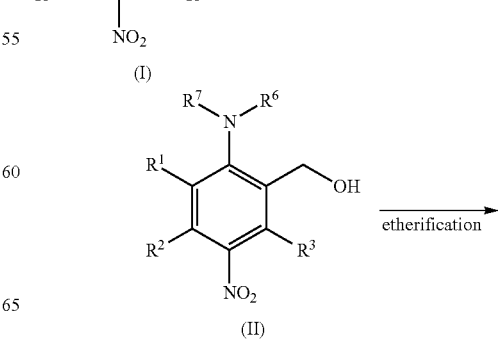

-continued

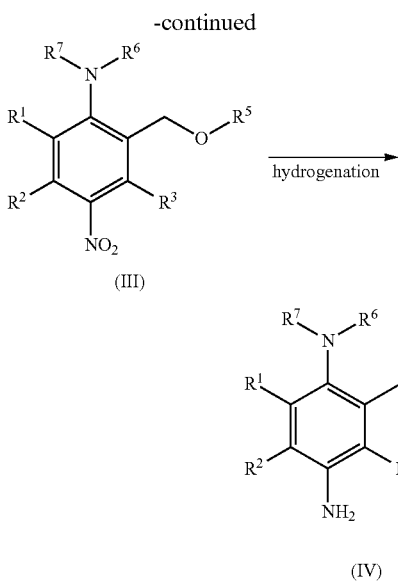

(IV-a), $R^1, R^2, R^3, R^6, R^7 = H$
$R^5 = CH_3$ wherein $R^1$, $R^2$, and $R^3$ are substituents selected from the group consisting of:
  i. C-linked substituents selected from the group consisting of:
     a) alkyl groups;
     b) aryl groups; and
     c) substituents selected from the group consisting of $COOA^1$, $CONA^1$, $CONA^1COA^2$, $C(=NA^1)NA^1A^2$, and CN;
        wherein the C-linked substituents comprise from 1 to about 10 carbon atoms and from 0 to about 5 heteroatoms selected from the group consisting of O, F, Cl, N, P, Si, and combinations thereof;
  ii. S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
  iii. O-linked substituents selected from the group consisting of $OA^1$, $ONA^1A^2$;
  iv. N-linked substituents selected from the group consisting of $NA^1A^2$; $(NA_1A^2A^3)^+$, $NA^1SA^2$, $NO_2$;
  v. halogens selected from the group consisting of F, Cl, Br, and I;
  vi. hydrogen; and
  vii. combinations thereof;
    wherein $A^1$, $A^2$, and $A^3$ are alkyl groups comprising from 1 to about 10 carbon atoms and from 0 to about 5 heteroatoms selected from the group consisting of O, F, Cl, N, P, Si, and combinations thereof;
wherein $R^5$ is an alkyl group; and
wherein $R^6$ and $R^7$ are selected from the group consisting of hydrogen, alkyl groups, aminoalkyl groups, hydroxyalkyl groups, and combinations thereof; and further comprising inserting a nitro function into anthranilic acid or compounds thereof in the presence of a nitrating agent and a solvent to prepare the compound of formula (I):

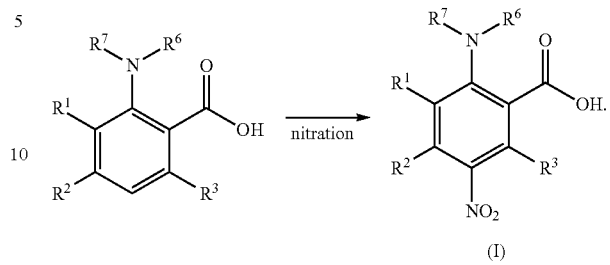

2. The process according to claim 1, wherein the carbonyl reduction of the compound of formula (I) into the compound of formula (II) is performed in the presence of a carbonyl reducing agent, a carbonyl reduction catalyst, and a solvent.

3. The process according to claim 2, wherein the carbonyl reducing agent is selected from the group consisting of hydrazine, hydrazine hydrate, $H_2$, $LiAlH_4$, $LiBH_4$, DIBAL-H, $NaBH_4$, $NaCNBH_3$, $B_2H_6$, $BH_3$/THF, sodium hydrosulfite, sodium sulfide, and combinations of thereof.

4. The process according to claim 2, wherein the carbonyl reduction catalyst is selected from the group consisting of nickel, palladium, Lindlar's catalyst, cobalt, copper chromite, platinium, platinum oxide, rhenium, tin(II) chloride, titanium(III) chloride, zinc, amarium, iron and combinations thereof.

5. The process according to claim 1, wherein the etherification of the compound of formula (II) into the compound of formula (III) is performed by alkylation in the presence of an alkylating agent, a phase transfer catalyst, a solvent, and a base.

6. The process according to claim 5, wherein the alkylating agent is selected from the group consisting of methanol, $(C_1$-$C_4)$—I, $(C_1$-$C_4)$—Br, $(C_1$-$C_4)$—Cl, $Me_2SO_4$, and combinations thereof.

7. The process according to claim 5, wherein the phase transfer catalyst is selected from the group consisting of tetrapentylammonium bromide, tetraoctylammonium chloride, tetraoctylammonium bromide, tetrahexylammonium iodide, tetrahexylammonium chloride, tetrahexylammonium bromide, tetraheptylammonium bromide, tetraethylammonium tetrafluoroborate, tetraethylammonium chloride, tetraethylammonium bromide, tetradodecylammonium tetrafluoroborate, tetradodecylammonium chloride, tetradodecylammonium bromide, tetradecyl-trimethylammonium chloride, benzyltriethyl ammonium chloride, phenyl-trimethylammonium bromide, octyl-trimethylammonium bromide, octadecyl-trimethylammonium chloride, octadecyl-trimethylammonium bromide, methyl-trioctylammonium iodide, and combinations thereof.

8. The process according to claim 5, wherein the base is selected from the group consisting of sodium hydroxide, potassium hydroxide, ammonium hydroxide, calcium hydroxide, magnesium hydroxide, barium hydroxide, aluminum hydroxide, ferrous hydroxide, ferric hydroxide, zinc hydroxide, lithium hydroxide, sodium bicarbonate, sodium carbonate, and combinations thereof.

9. The process according to claim 1, wherein the etherification of the compound of formula (II) into the compound of formula (III) is performed by a condensation reaction in the presence of a condensation catalyst and a solvent.

10. The process according to claim 9, wherein the condensation catalyst is selected from the group consisting of mineral acids, Lewis Acids, aluminum chloride, titanium tetraisopropoxide, and combinations thereof.

11. The process according to claim 1, wherein the hydrogenation of the compound of formula (III) into the compound of formula (IV) is performed in the presence of hydrogen, a hydrogenation catalyst, and a solvent.

12. The process according to claim 11, wherein the hydrogenation catalyst is selected from the group consisting of, nickel, palladium, Lindlar's catalyst, cobalt, copper chromite, platinium, platinum oxide, rhenium, tin(II) chloride, titanium(III) chloride, zinc, samarium, iron and combinations thereof.

13. The process according to claim 1 further comprising transforming the compound of formula (IV) into the salt of formula (V) in the presence of mHZ and a solvent:

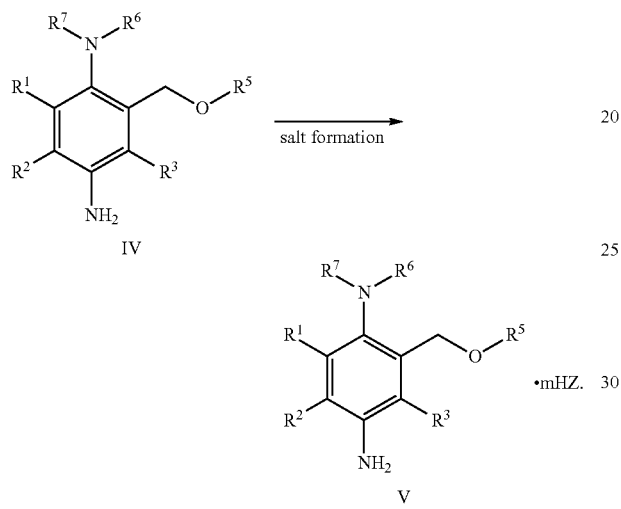

14. The process according to claim 13, wherein HZ is selected from the group consisting of D,L-malic acid, L-malic acid, D-malic acid, hydrochloric acid, hydrobromic acid, citric acid, acetic acid, lactic acid, succinic acid, tartaric acid, sulfuric acid, and combinations thereof; and wherein m =1.

15. The process according to claim 1, wherein the carbonyl reduction, then etherification, and then hydrogenation are performed successively.

16. The process according to claim 1 comprising:
   a. reducing a carbonyl group of 5-nitroanthranilic acid (I-a) to prepare 2-amino-5-nitrobenzyl alcohol (II-a):

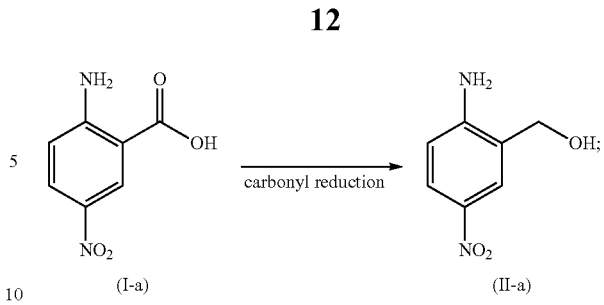

b. performing the etherification of 2-amino-5-nitrobenzyl alcohol (II-a) to prepare 2-methoxymethyl-4-nitroaniline (III-a):

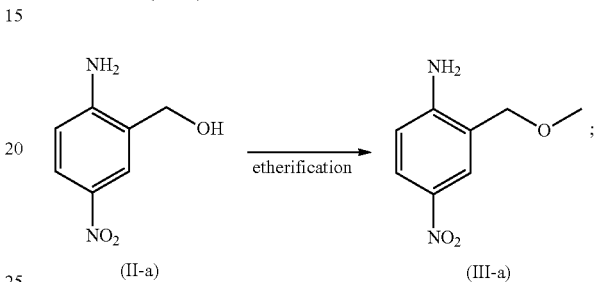

and
   c. hydrogenating 2-methoxymethyl-4-nitroaniline (III-a) to prepare 2-methoxymethyl -[1,41]-benzenediamine (IV-a):

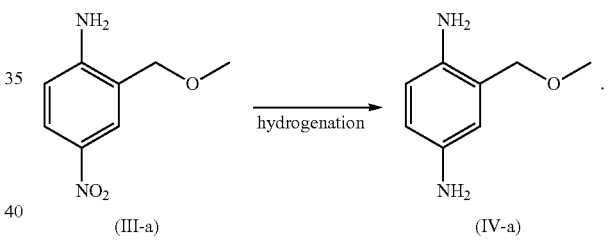

17. The process according to claim 16, wherein reducing the carbonyl group is performed at a temperature from about 50° C. to about 80° C.

18. The process according to claim 17, wherein the etherification is performed by phase transfer alkylation.

* * * * *